United States Patent [19]

Cure et al.

[11] Patent Number: 5,068,039

[45] Date of Patent: Nov. 26, 1991

[54] METHOD AND DEVICE FOR DISPERSING IONS BY REMOTE ACTION

[76] Inventors: Jorge Cure, 8201 NW. 191 La., Miami, Fla. 33015; Panagiotis T. Pappas, Marcopuliotis 26, G-11744, Athens, Greece; Harry Eichler, 5323 Hayes St., Hollywood, Fla. 33021

[21] Appl. No.: 446,984

[22] Filed: Dec. 6, 1989

[30] Foreign Application Priority Data

Sep. 20, 1989 [GR] Greece ............................ 890100595

[51] Int. Cl.[5] ............................................ B01D 35/06
[52] U.S. Cl. .................................... 210/695; 210/222; 361/143
[58] Field of Search ................ 210/222, 695; 204/155; 435/173; 436/177; 361/143, 159, 234; 422/22; 426/237; 164/466, 498

[56] References Cited

U.S. PATENT DOCUMENTS

| | | | |
|---|---|---|---|
| 2,736,843 | 2/1956 | Douglas et al. | 361/159 |
| 3,337,776 | 8/1967 | Elmi | 361/143 |
| 3,703,958 | 11/1972 | Kolm | 210/695 |
| 4,369,345 | 1/1983 | Czerlinski | 219/10.491 |
| 4,458,153 | 7/1984 | Wesley | 422/22 |
| 4,818,697 | 4/1989 | Liboff et al. | 435/173 |
| 4,938,875 | 7/1990 | Niessen | 210/222 |

FOREIGN PATENT DOCUMENTS

WO/8805763  8/1988  PCT Int'l Appl. .

*Primary Examiner*—W. Gary Jones
*Assistant Examiner*—Matthew O. Savage
*Attorney, Agent, or Firm*—Herbert L. Lerner; Laurence A. Greenberg

[57] ABSTRACT

The device acts by remote action to disperse electric charges or ionic concentrations inside organic or inorganic matter, inside biological matter, or in any other matter in which mobile electric charges exist. The remote action charge transport takes place without direct contact with the matter. The main characteristic resides is in a particular direction or one way motion of the charges from a particular region. The device is useful for charging or discharging regions within bulk matter where electrical contact is either difficult or impossible to establish. The device is also ideal in applying Nordenstrom's method in medicine, where electrical circuits are established between particular regions by inserting electrodes into these regions.

4 Claims, 3 Drawing Sheets

METHOD AND DEVICE FOR DISPERSING IONS BY REMOTE ACTION

BACKGROUND OF THE INVENTION

1. Field of the Invention

The invention relates to a method and device for dispersing ions by remote action.

2. Description of the Related Art

In recent years a great number of researchers have been paying much attention to biological effects induced by electromagnetic fields. Such fields affect the transmembrane potential of cells changing the ionic concentration in and out of the same. This is seen, for example, from Szent-Gyorgyi, Introduction to a Submolecular Biology (Academic Press, NY, 1960); Szent-Gyorgyi, Bioelectronics (Academic Press, NY, 1968); Szent-Gyorgyi, Electronic Biology (Marcel Dekker, Inc., NY 1976); Cone, C. D., J. Theoret. Biol., 30, 151-181 (1971); Cone, C.D., Ann. New York Acad. Sci., 238, 420-435 (1974); Cone, C.D., Transmembrane Potentials and Characteristics of Immune and Tumor Cells (CRC Press, Inc., Boca Raton, Fla., 1985) Ch. 9, p. 138-141; Albert, B., Bray, D., Lewis, J., Raff, M., Roberts, K., and Watson, J. D., Molecular Biology of the Cell (Garland Publishing, Inc., NY, 1983); Nordenstrom, B., Biologically Closed Electric Circuits (Nordic Medical Publications, Stockholm, 1983); Barothy, J. M., Biological Effects of Magnetic Fields (Plenum Press, NY, 1964) p. 100-108; Cure, J.C., Phys. Lett., 116b, no. 2.3, 158-160 (1982); and Cure, J.C., Northeastern University, Boston, November 1987 (Private Communication).

More than 40 years ago Szent-Gyorgyi observed the importance of the ratio D/A in the cells, wherein D stands for substances that donate electrons, while A stands for substances that accept electrons. This is seen, for example, from the three publications by Szent-Gyorgyi mentioned above. He observed that when $D/A \approx 1$, the cells remain in the resting phase. On the other hand when $D/A > 1$, the cells go into the miotic phase. Szent-Gyorgyi also observed experimentally that the introduction of accepters in the blood stream of mice with a particular type of cancerous tumors, arrested the growth of the same. The introduction of donors in the body of the affected organism do not produce any significant effect because the cells are rich in donors. These concepts bear a close relationship with Cone's theoretical and experimental conclusions. Cone observed that the cells remain in the resting phase when the transmembrane potential is approximately $-65$ mv. Nevertheless when the cells are in constant proliferation this potential changes to approximately $-15$ mv.

Recently Nordenstrom has reported successful electric treatment of cancerous tumors. His method takes the form of inserting a positive electrode in the core of the tumor while the negative one is inserted outside the cancerous tumor. There is no doubt that the electric field, provided by a 10 v DC battery, disperses the ions in the cancerous region of the tumor. The positive electrode also plays the role of a physical accepter A instead of the chemical ones used in chemotherapy. The dispersion or concentration of ions by electrostatic fields seems to have no significant effects. Other than an initial charge transportation, an electrostatic field may cause practically no substantial electrical current which is necessary for an electrolytic dispersion or neutralization of ions. On the other hand the effect of alternating electric fields have no substantial results, because of the alternating dispersion and concentration of ions. Nevertheless, recently many reports have been published concerning the biological effects of alternating fields of very low frequency. The use of static magnetic fields is known to have no effect on static distributions of charges or ions. However, from a biophysical point of view, reports are known that this type of field can arrest the growth of cancerous tumors. The use of alternating magnetic fields causes effects similar to the alternating electric fields, inducing oscillating dispersion and concentration of electric charges, causing an alternating electromotive force $E = kdB/dt = k'di/dt$, in such a way as to cause no net effect as far as ion dispersion or ion concentration is concerned.

SUMMARY OF THE INVENTION

It is accordingly an object of the invention to provide a method and device for dispersing ions by remote action, which overcomes the hereinafore-mentioned disadvantages of the heretofore-known devices of this general type.

With the foregoing and other objects in view there is provided, in accordance with the invention, a device for removing ions and/or electrical charges inside materials by remote action, comprising first means for producing magnetic flux being spaced from a material from which ions and/or electrical charges are to be removed, second means surrounding the material for eliminating and/or smoothing the negative (decreasing) phase of the magnetic flux, and means for short circuiting the second means.

The first means may be a first electrically powered coil, the second means may be a second coil, and the short circuiting means may be a diode short circuiting the second coil.

In accordance with another feature of the invention, the coils are connected together or the coils form one coil or one of the coils is part of the other of the coils.

In accordance with a further feature of the invention, the diode is a rectifying diode.

In accordance with an added feature of the invention, there is provided a first movable arm on which the first coil is disposed, a second arm on which the second coil is disposed, a surface below the second coil for supporting the material, and means for supplying electrical power to the first coil.

In accordance with a concomitant feature of the invention, there is provided a capacitor filter connected to the electrical power supplying means, a rheostat connected to the capacitor filter, a capacitor bank connected to the rheostat, and a spark gap disposed between the capacitor bank and the first coil.

With the objects of the invention in view there is also provided a method for removing ions and/or electrical charges inside materials by remote action, which comprises producing magnetic flux with a first electrically powered coil spaced from a material from which ions and/or electrical charges are to be removed, surrounding the material with a second coil spaced from said first coil and short circuited by a diode, and eliminating and/or smoothing the negative (decreasing) phase of the magnetic flux with the second coil.

An advantage of the invention proposed herein is that of being non-invasive, making its application ideal to disperse ions in biological matter.

Other features which are considered as characteristic for the invention are set forth in the appended claims.

Although the invention is illustrated and described herein as embodied in a method and device for dispersing ions by remote action, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

Figure 1:
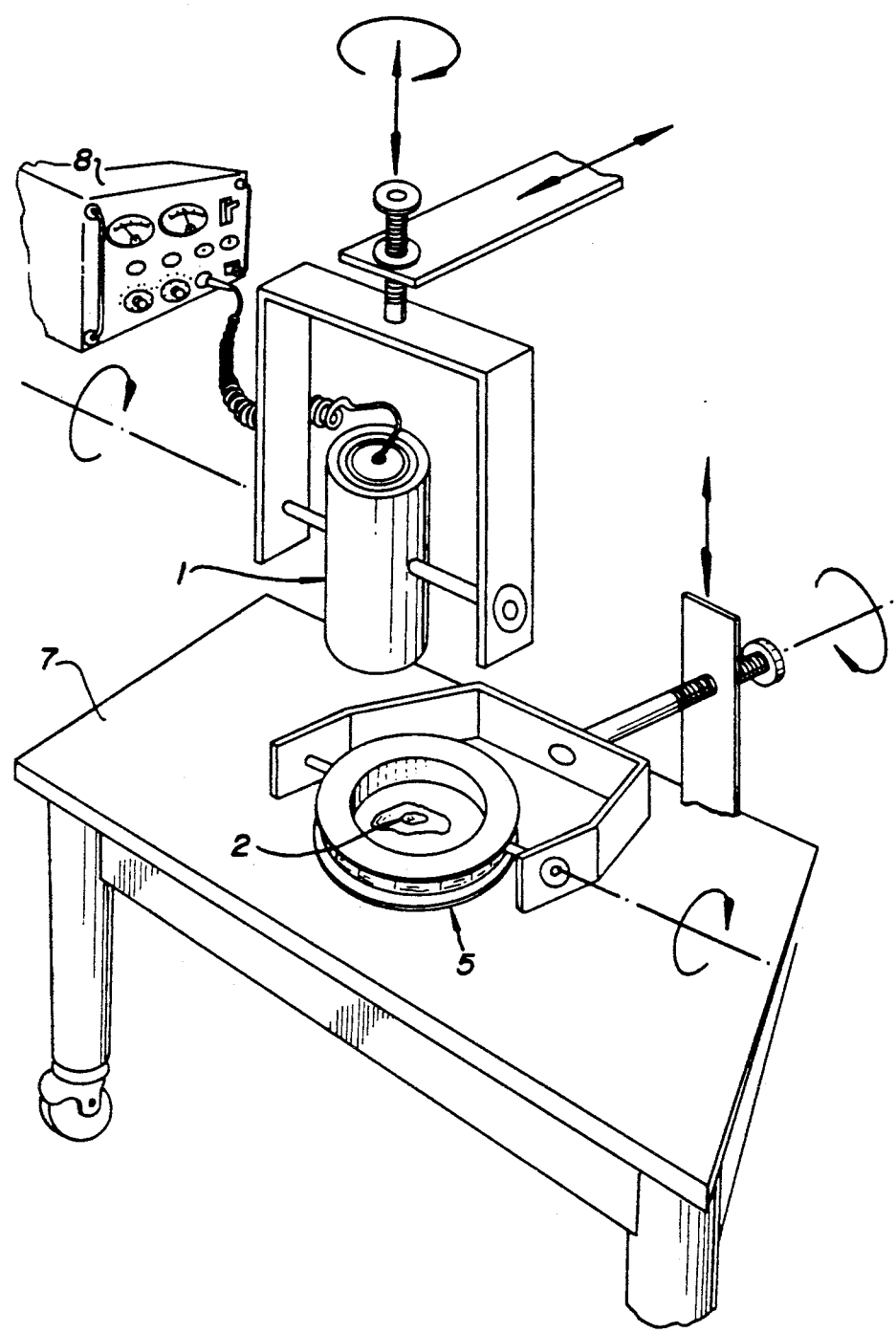
FIG. 1 is a fragmentary, diagrammatic, perspective view of the remote action ion dispersing device according to the invention.
Figure 2:
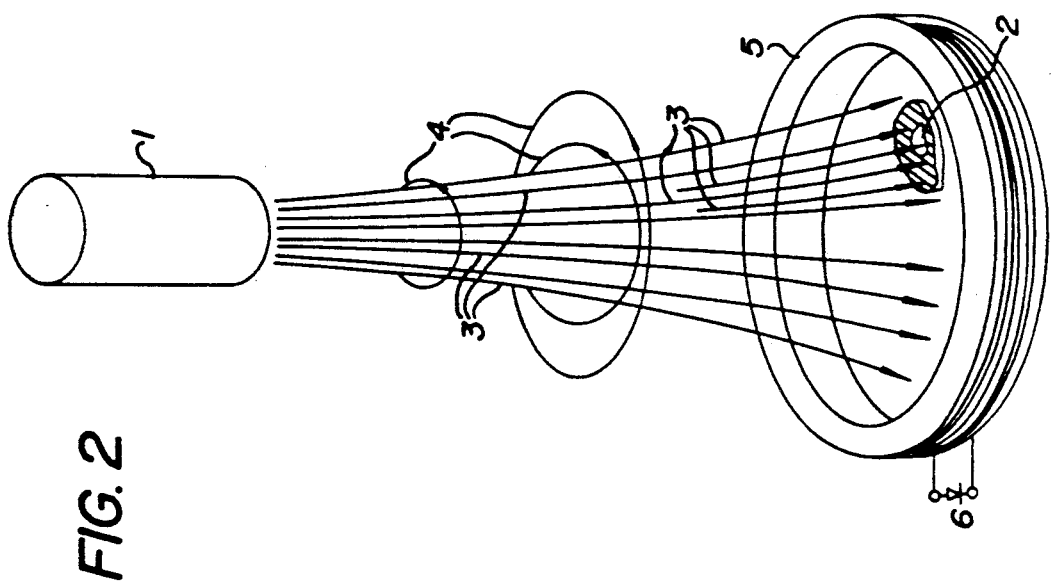
FIG. 2 is a perspective view of part of the device of FIG. 1 showing the magnetic lines.

Referring now to the figures of the drawings in detail and first, particularly, to FIG. 1 thereof, there is seen a first main coil 1 which is mounted on an arm that is movable in the direction of the arrows and to which an intermittent current is supplied with a fast rise time, i.e., a square or triangular pulse, from an electrical source 8 or from the discharge current of a charged capacitor. A movable table 7 made of insulating material is disposed above or below the coil 1. A material or the object containing a region 2 in which ions are to be dispersed is disposed on top of the table 7. As seen in FIGS. 1 and 2, the coil 1 is accordingly located in such a way that its magnetic lines B, which have been given reference numeral 3, pass through the region 2, or in other words the region 2 is placed close to the perimeter of a concentric magnetic potential A of the coil 1, which has been given reference numeral 4. A second coil 5, which is also mounted on an arm that is movable in the direction of the arrows, surrounds the region 2 in such a way that the plane of the coil 5 perpendicularly cuts the magnetic lines B given reference numeral 3, i.e., the turns of the coil 5 are parallel to the magnetic potential A given reference numeral 4, as seen in FIGS. 1 and 2. The coil 5 is short circuited with a fast recovery, high tension and high power diode 6. The polarity of the diode 6 depends on the direction of the current which is desired to be induced in the region 2. The current in the region 2 is opposite to the current in the coil 5, which corresponds to the conducting current in the diode 6. The polarity of the coil 1 is chosen in such a way as to have the initial current thereof opposite to the desired induced current in the region 2.

Figure 5:
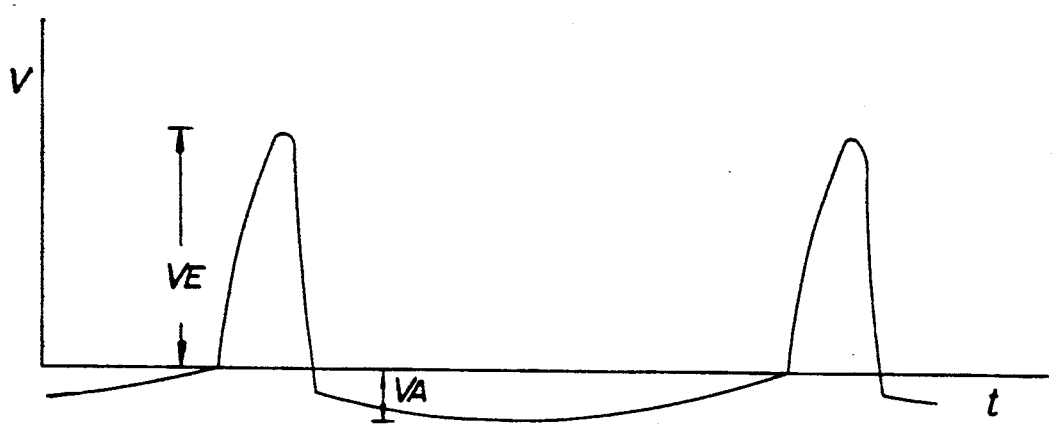
FIG. 5 is a graph of the potential induced by the device.

The function of the device is as follows: When a high surge voltage is supplied to the coil, then a rapidly rising current flows. At the same time an induced current appears on every conducting surface, or in every conducting volume, that opposes the increase of the magnetic flux in the coil 1, according to The Lenz Rule of Electromagnetism. During this phase, the coil 5 remains inactive, because the diode 6 connected thereto is polarized not to conduct. However, ions are displaced towards a particular direction in the region 2 from which they are desired to be dispersed. Immediately after this, and as a rule, the current in the coil 1 will be set into oscillations that will depend on the frequency of the natural resonance thereof. During those periods, the current in the coil 1 will be decreasing. The coil 5 will start conducting a current again to maintain the existing magnetic flux, according to The Lenz Rule. In this way, the coil 5 considerably delays the fall of the initial flux through the region 2 while the coil 1 continues to execute damping oscillations. Finally, the magnetic flux through the region 2 will fall to zero, after a time which will mainly depend on the self inductance and resistance of the coil 5: $t \simeq L/R$. In this way, by choosing a small self inductance L for the coil 1, a power supply of a high surge voltage "with low internal resistance", and a high self inductance L and low resistance R for the coil 5, it is possible to induce a high voltage $V_E$ in the region 2 and in a particular direction (for a short duration), as well as any small induced voltage $V_A$ in the opposite direction (for a longer duration), according to the diagram of FIG. 5. In this way, it is possible to transfer an amount of charge in the direction which the high and short duration induced potential $V_E$ determines, practically without expecting the return of the charges in the opposite direction, if the small, long duration and oppositely induced potential $V_A$ is kept below the threshold electrolytic potential which confined the initial charge or ion concentration.

In general, the device is expected to operate effectively as a "DC inductor" or "DC transformer", so to speak, with respect to any non-linearly conducting medium, (or medium with non-constant ohmic resistance), by appropriately choosing the parameters of the coils 1 and 5, as well as the voltage and internal resistance of the power supply. The amount of transported charges increases with the repetition of the function cycle of the device, i.e. by repeating the voltage surges in the coil 1. Therefore, the transported or dispersed charge is a function of the time of operation of the device.

Figure 3:
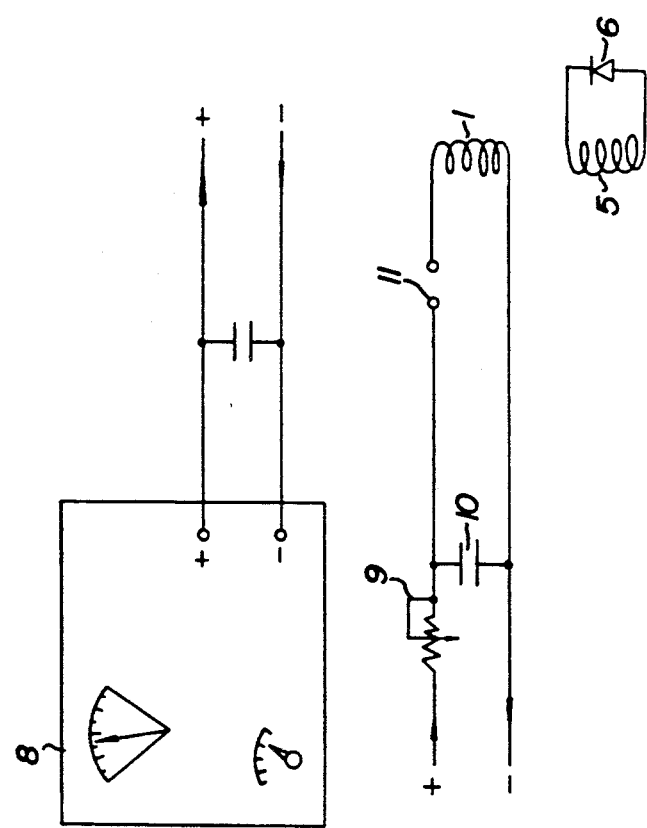
FIG. 3 is an equivalent schematic circuit diagram of the device.

A description of a particular embodiment of the invention is as follows: The electrical diagram of the working model of the device is given in the FIG. 3. The electrical source or power supply 8 is formed of an adjustable source of voltage supplying 500 to 16,000 volts and a capacitor filter of 1 uF, 20 kv. The power supply is connected through a rheostat 9, to the main device which is formed of a specially constructed capacitor bank 10, which has the following characteristics: very fast discharge time, very high power, very low internal resistance and parasitic self inductance, and is made of two cooper sheets which are 0.3 mm thick, 1 $m^2$ in area and are separated by a sheet of glass which is 3 mm thick and has the same area, as well as a spark gap 11 with an adjustable gap distance, that are connected as shown in the diagram of FIG. 3. The coil 1 is formed of several turns which are 40 cm in diameter of insulated copper wire being 4 mm in diameter. The coil 5 is formed of about 1000 turns of 80 cm in diameter of enamel copper wire being 2 mm in diameter.

Figure 4:
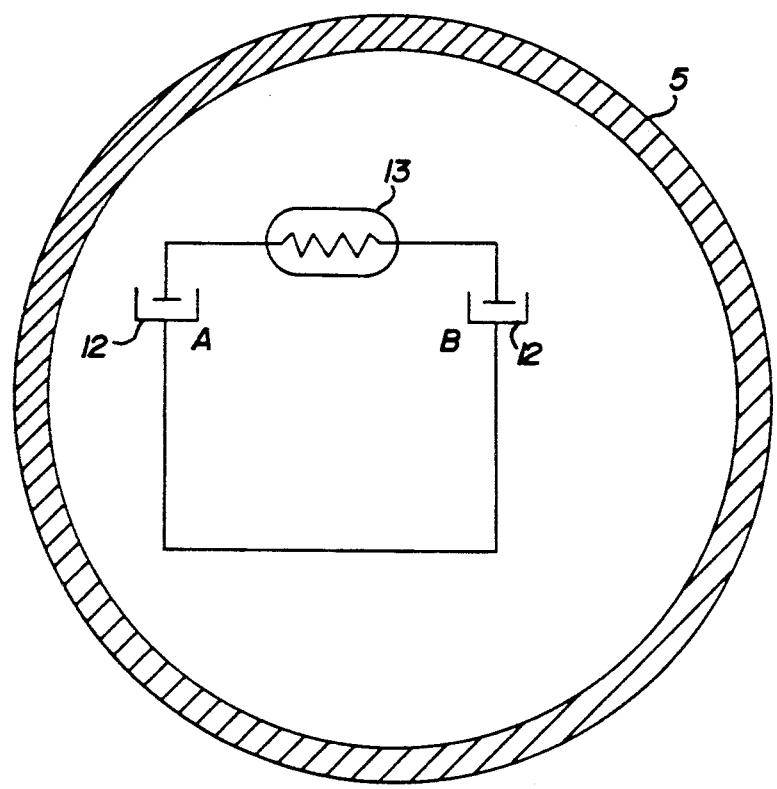
FIG. 4 is a cross-sectional view of the coil of the device with an equivalent schematic circuit diagram.

A sample object used in one of the examples or trials for dispersing the ions thereof, is formed of two small uncharged capacitors A and B of 1 uF given reference numeral 12, which are connected through a non-linear resistor or varistor 13 as shown in FIG. 4 and placed inside the coil 5 at a distance of 50 cm from the coil 1.

The power supply was adjusted to charge the capacitor 10 causing arc discharge in the spark gap 11 approximately every 0.3 seconds. After 3 minutes of operating the device, the capacitors A and B given reference numeral 12 were immediately measured with a volt meter. The capacitor A was found charged in the forward direction by several tenths of a volt and the capacitor B in the reverse direction by several hundredths of a volt. The difference in the charges is explained by the expected dielectric leakage of the capacitor B, charged in the reverse direction. When removing the coil 5 or the diode 6, no systematic charge was found in the capacitors A and B, contrary to what was observed before. The difference was distinct and considerable. When inverting the polarity of the diode 6 in the coil 1, the charges in the capacitors A and B were always found to be inverted. (The induced charges were characteristic of the device and not of the sample circuit excluding the possibility that rectification took place in the sample circuit).

The advantages of the device are the following: The basis of the operation thereof is the production of the waveform of the induced potential in the diagram of FIG. 5. It appears as though the production of such a waveform with another electronic device is not possible or easy, because a considerably large power of several K watts is required for substantial results in practice. In such a case, any coil which would have the power to produce a predetermined form of magnetic flux, would carry parasitic oscillations or would have produced unwanted components of tension in the induced potential.

Mainly, these unwanted side effects are suppressed by the use of the coil 5 with the short-circuited diode 6. The effectiveness of the coil 5 and the diode 6 is so great that regardless of the form of magnetic flux which the coil 1 is producing, the induced potential in the region 2 is almost always of the desired form in the diagram of FIG. 5. The coil 1 may even be powered by a perfect sinusoidal tension of a definite frequency (i.e. it may be powered with the mains frequency, or by a power of a much higher frequency), for avoiding nearby unwanted interference, with satisfactory results for the induced tension in the region 2.

Some of the advantages of the device according to the invention are the following: The induced tension of the diagram of FIG. 5 appears only near the region 2 and not all over the effective space surrounding the coil 1, where it would cause unwanted induced DC induction to the operators of the device or to other objects outside the region 2. The power which the coil 5 and the diode 6 absorb, is a small fraction of the power of the coil 1 (of several Kwatts). In this way, the coil 5 and the diode 6 with the high requirements thereof may easily cope with the stress of a much lower power. On the other hand, the field of the coil 1 is modified to the minimum required degree, which will cause minimum interference in the case of a sinusoidal power supply. Finally, with respect to particular applications for transporting or dispersing ions, the device according to the invention is clearly superior for it requires no invasion or entry into the region 2, such through the use of electrodes or chemical substances, for example.

The expected applications extend to a large spectrum of technology and science, where charge or ion transport is required to occur in regions which are not easily accessible, in biology, medicine, the chemical industry, Electrolysis, electrolytic metal plating, electrolytic casting, direct current power supply and energy, without using direct contacts, or in general, where a DC transformer, or a DC inductor, is required.

We claim:

1. Device for dispersing or transporting ions and/or electrical charges inside a material containing dispersible or transportable ions and/or electrical charges by remote action, comprising a first electrically powered coil spaced from the material from which ions and/or electrical charges are to be dispersed or transported, said first coil producing magnetic flux, a second coil surrounding the material and being separated from said first coil by a plane perpendicular to a longitudinal axis of said first coil, for eliminating and/or smoothing the negative phase of the magnetic flux, and a short circuit across said second coil consisting of a rectifying diode for allowing dc current to flow in said second coil.

2. Device according to claim 1, including a first movable arm on which said first coil is disposed, a second arm on which said second coil is disposed, a surface below said second coil for supporting the material, and means for supplying electrical power to said first coil.

3. Device according to claim 1, including a capacitor filter connected to said electrical power supplying means, a rheostat connected to said capacitor filter, a capacitor bank connected to said rheostat, and a spark gap disposed between said capacitor bank and said first coil.

4. Method for dispersing or transporting ions and/or electrical charges inside materials by remote action, which comprises producing magnetic flux with a first electrically powered coil spaced from a material from which ions and/or electrical charges are to be dispersed or transported, surrounding the material with a second coil separated from said first coil by a plane perpendicular to a longitudinal axis of said first coil and connecting a short circuit across said second coil consisting of a diode for eliminating and/or smoothing the negative phase of the magnetic flux with the second coil.

* * * * *